United States Patent [19]

Breuer et al.

[11] 4,088,815
[45] * May 9, 1978

[54] 3-HETEROTHIO-7-UREIDO CEPHALOSPORINS

[75] Inventors: Hermann Breuer; Uwe D. Treuner, both of Regensburg, Germany

[73] Assignee: E. R. Squibb & Sons, Inc., Princeton, N.J.

[*] Notice: The portion of the term of this patent subsequent to Dec. 7, 1993, has been disclaimed.

[21] Appl. No.: 664,795

[22] Filed: Mar. 8, 1976

Related U.S. Application Data

[63] Continuation-in-part of Ser. No. 507,906, Sep. 20, 1974, abandoned.

[51] Int. Cl.² ............................................. C07D 501/36
[52] U.S. Cl. .................................... 544/26; 424/246
[58] Field of Search .................... 260/243 C; 544/26

[56] References Cited

U.S. PATENT DOCUMENTS

| | | | |
|---|---|---|---|
| 3,641,021 | 2/1972 | Ryan | 544/217 |
| 3,673,183 | 6/1972 | Erickson | 544/30 |
| 3,708,479 | 1/1973 | Welch et al. | 260/243 C |
| 3,757,015 | 9/1973 | Crast | 544/217 |
| 3,759,904 | 9/1973 | Crast | 544/26 |
| 3,796,801 | 3/1974 | Guarini | 424/246 |
| 3,813,388 | 5/1974 | Crast | 544/26 |
| 3,819,621 | 6/1974 | Morimoto | 544/26 |
| 3,833,568 | 9/1974 | Dolfini et al. | 424/246 |
| 3,860,591 | 1/1975 | Breuer | 544/30 |
| 3,867,380 | 2/1975 | Dunn et al. | 544/26 |
| 3,867,380 | 2/1975 | Dunn et al. | 260/243 C |
| 3,878,204 | 4/1975 | Ochiai et al. | 544/25 |
| 3,925,368 | 12/1975 | Cooper et al. | 260/243 C |
| 3,996,217 | 12/1976 | Breuer et al. | 260/243 C |

*Primary Examiner*—Donald G. Daus
*Assistant Examiner*—David E. Wheeler
*Attorney, Agent, or Firm*—Lawrence S. Levinson; Merle J. Smith; Stephen B. Davis

[57] ABSTRACT

Compounds of the formula

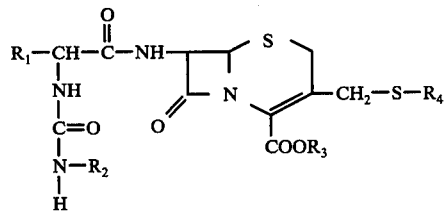

wherein $R_1$ is hydrogen, lower alkyl, cycloalkyl, cycloalkenyl, cycloalkadienyl, phenyl, phenyl-lower alkyl and substituted phenyl and phenyl-lower alkyl; $R_2$ is hydrogen or lower alkyl; $R_3$ is hydrogen, lower alkyl, phenyl-lower alkyl, substituted phenyl-lower alkyl, diphenyl-lower alkyl, tri(lower alkyl)stannyl, tri(lower alkyl)silyl, a salt forming ion, or the group

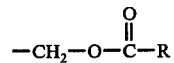

wherein R is lower alkyl, phenyl, phenyl-lower alkyl, or substituted phenyl and phenyl-lower alkyl; and $R_4$ represents certain heterocyclic groups are disclosed. These compounds are useful as antibacterial agents.

8 Claims, No Drawings

3-HETEROTHIO-7-UREIDO CEPHALOSPORINS

This application is a continuation-in-part of Ser. No. 507,906 filed on Sept. 20, 1974, now abandoned.

BACKGROUND OF THE INVENTION

Cephalosporins having a ureido acyl side chain are disclosed in U.S. Pat. Nos. 3,673,183; 3,708,479; 3,833,568; and 3,860,591. Cephalosporins substituted in the 3-position with -CH$_2$-S-hetero groups and in the 7-position with

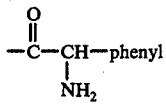

groups are disclosed as possessing anti-bacterial activity in U.S. Pat. Nos. 3,641,021; 3,759,904; 3,813,388; 3,878,204; 3,796,801 (method of treating Enterobacter infections), etc. Also disclosed as useful intermediates are cephalosporins substituted in the 3-position with -CH$_2$-S-hetero groups and in the 7-position with a

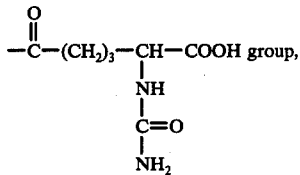

U.S. Pat. No. 3,819,621.

SUMMARY OF THE INVENTION

This invention relates to new cephalosporins of the formula

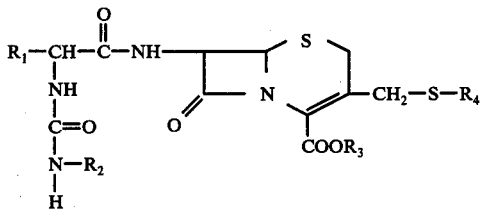

(I)

R$_1$ is hydrogen, lower alkyl, cycloalkyl, cycloalkenyl, cycloalkadienyl, phenyl, phenyl-lower alkyl or substituted phenyl and phenyl-lower alkyl; R$_2$ represents hydrogen or lower alkyl, and R$_3$ represents hydrogen, lower alkyl, phenyl-lower alkyl, diphenyl-lower alkyl, substituted phenyl-lower alkyl, tri(lower alkyl)stannyl, tri(lower alkyl)silyl, a salt forming ion, or the group

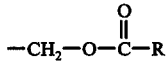

wherein R is lower alkyl, phenyl, phenyl-lower alkyl, or substituted phenyl and phenyl-lower alkyl; and R$_4$ represents certain heterocyclic groups.

DETAILED DESCRIPTION OF THE INVENTION

The various groups represented by the symbols have the meaning defined below and these definitions are retained throughout this specification.

The lower alkyl groups referred to throughout this specification include straight or branched chain hydrocarbon groups containing 1 to 8 carbon atoms, preferably 1 to 4 carbons. Examples of the type of groups contemplated are methyl, ethyl, propyl, isopropyl, butyl, t-butyl, etc. The lower alkoxy groups include such lower alkyl groups attached to an oxygen, e.g., methoxy, ethoxy, propoxy, etc. The phenyl-lower alkyl and diphenyl-lower alkyl groups include such lower alkyl groups attached to a phenyl, e.g., benzyl, phenethyl, diphenylmethyl, etc.

Cycloalkyl refers to groups having 3 to 7 carbons in the ring, i.e., cyclopropyl, cyclobutyl, cyclopentyl, cyclohexyl, and cycloheptyl. The term cycloalkenyl also represents rings having 3 to 7 carbons with one double bond, i.e., cyclobutenyl, cyclopentenyl, cyclohexenyl, etc. The term cycloalkadienyl represents a ring having 6 or 7 carbons with two double bonds located at various positions such as 1,4-cyclohexadienyl which is preferred.

The substituted phenyl and substituted phenyl-lower alkyl groups representing R$_1$, R$_3$, or R include one or two (preferably only one) simple substituents selected from halogen (preferably chlorine or bromine), lower alkyl and lower alkoxy, e.g. 2-, 3- or 4-chlorophenyl, 2-, 3- or 4-bromophenyl, 3,4-dichlorophenyl, 2-methylphenyl, 4-ethoxyphenyl, 2-, 3-, or 4-chlorobenzyl, 2-, 3- or 4-ethylphenethyl, etc. Also, in the case of R$_1$, the phenyl substituent can be a hydroxyl group.

The salt forming ions represented by R$_3$ may be metal ions, e.g., aluminum, alkali metal ions such as sodium or potassium, alkaline earth metal ions such as calcium or magnesium, or an amine salt ion, of which a number are known for this purpose, for example, phenyl-lower alkylamines such as dibenzylamine, N,N-dibenzylethylenediamine, lower alkylamines such as methylamine, triethylamine, and N-lower alkylpiperidines such as N-ethylpiperidine.

The heterocyclic groups represented by R$_4$ are

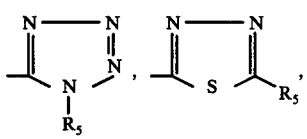

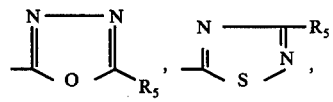

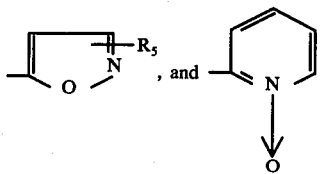

wherein $R_5$ is hydrogen or alkyl of 1 to 4 carbons.

Preferred embodiments of this invention are as follows:

$R_1$ is phenyl, benzyl, phenethyl, substituted phenyl, benzyl or phenethyl, cyclohexenyl or 1,4-cyclohexadienyl.

$R_2$ is hydrogen or lower alkyl of 1 to 4 carbons.

$R_3$ is hydrogen, lower alkyl of 1 to 4 carbons, benzyl, phenethyl, diphenylmethyl, trimethylsilyl, trimethylstannyl, aluminum, alkaline earth metal, alkali metal, or

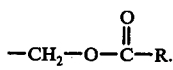

R is lower alkyl of 1 to 4 carbons, phenyl, benzyl, or phenethyl.

The most preferred embodiments are:
$R_1$ is phenyl or 4-hydroxyphenyl, especially phenyl.
$R_2$ is hydrogen or methyl, especially hydrogen.
$R_3$ is hydrogen, sodium or potassium, especially hydrogen.

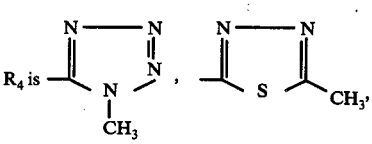

especially 5-methyl-1,3,4-thiadiazol-2-yl and 1-methyl-1H-tetrazol-5-yl.

Compounds of formula I are obtained by reacting an α-ureido compound of the formula

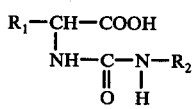

with a 3-heterothio-7-amino substituted cephalosporin of the formula

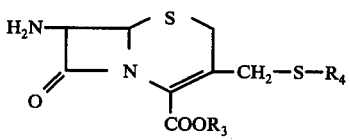

wherein $R_3$ is preferably diphenylmethyl or t-butyl or other ester protecting groups.

This reaction is carried out by converting the α-ureido compound of formula II to a mixed carbonic or other anhydride by treating a solution of the α-ureido compound in an organic solvent containing a tri(lower alkyl)amine with an anhydride forming agent, i.e., a lower alkyl chloroformate, an aryl chloroformate, or an acyl halide, at reduced temperatures of from about 0° C to about −20° C.

Alternatively, the α-ureido compound of formula II can be converted to an activated ester by reacting with a carboxyl group activating agent such as dicyclohexylcarbodiimide or bisimidazole carbonyl. In some cases the carboxyl group may be activated by conversion to an acid halide, e.g. the chloride, or to an azide.

The methods of preparing the α-ureido compounds of formula II are known to those skilled in the art.

The compounds of formula I can also be prepared by acylating the compound of formula III with an acid chloride of formula

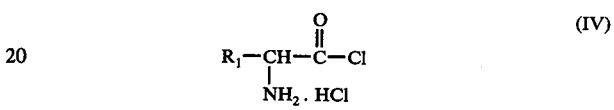

or an α-(substituted)amino acid of the formula

wherein Y is a protecting group such as

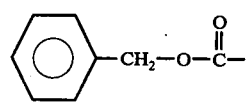

or

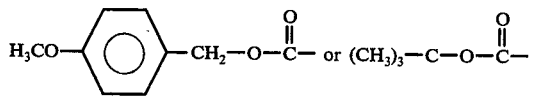

to yield after removal of the protecting group the intermediate of formula

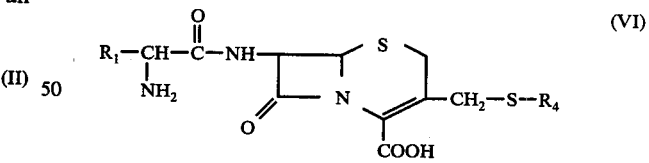

Various intermediates of formula VI where $R_1$ is phenyl are disclosed in U.S. Pat. Nos. 3,813,388; 3,641,021; 3,759,904; and 3,796,801.

The intermediates of formula VI are converted to the final products of formula I by treatment with an isocyanate of the formula

or when $R_2$ is hydrogen an alkali or alkaline earth cyanate such as potassium cyanate in solution at a pH of from about 7 to about 8.

The final products of formula I can also be prepared by reacting the compound of formula II with 7-ACA preferably in the presence of dicyclohexylcarbodiimide to yield the compound of formula VIII (as disclosed in U.S. Pat. No. 3,673,183)

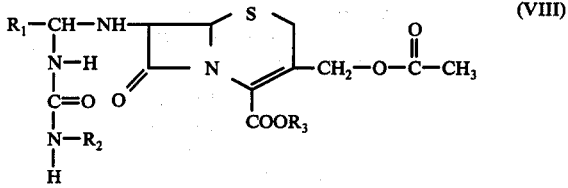 (VIII)

followed by treatment with the compound of the formula

 (IX)

$R_4$-S-H in solution at a pH of from about 7.8 to about 8.0.

Similarly, the final products of formula I can be prepared by reacting the compounds of formula IV or V with an ester of 7-ACA preferably in the presence of dicyclohexylcarbodiimide followed by treatment with an acid (HX), preferably trifluoroacetic acid in the presence of anisole, to yield the salt of formula

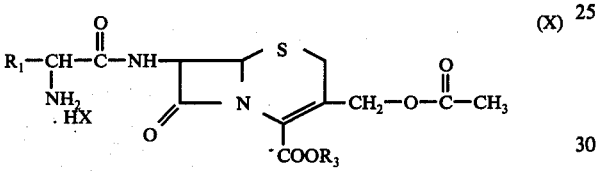 (X)

The salt of formula X is treated with the isocyanate of formula VIII (or the alkali or alkaline earth cyanate where $R_2$ is hydrogen) followed by treatment with the compound of formula IX to yield the final product of formula I.

The compounds of formula I wherein $R_3$ is lower alkyl, phenyl-lower alkyl, substituted phenyl-lower alkyl, diphenyl-lower alkyl, or the acyloxymethyl group

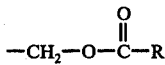

may be obtained by reacting the 3-heterothio-7-amino substituted cephalosporin of formula III or the 7-ACA either before or after the acylation of the 7-amino substituent with one or two moles of a compound of the formula

 (XI)

or

 (XII)

wherein halo is preferably chlorine or bromine in an inert solvent such as dimethylformamide, acetone, dioxane, benzene, or the like at about ambient temperature or below.

Similarly, the compounds of formula I wherein $R_3$ is tri(lower alkyl)stannyl or tri(lower alkyl)silyl are obtained by introducing such groups onto the 3-heterothio cephalosporanic acid moiety either before or after the acylation reaction.

The carboxylate salts of the compound of formula I are formed by reacting the carboxyl group of the cephalosporanic acid moiety, i.e., $R_3$ is hydrogen, with any of the salt forming ions described above.

It will be appreciated that the compounds of formula I are optically active due to the presence of an asymmetric carbon atom in the 7-position side chain. By selection of the appropriate starting material it is possible to obtain the compounds of formula I as a mixture of optically active isomers or isolated as a single isomer. The various isomers as well as their mixtures are within the scope of this invention.

The compounds of formula I have a broad spectrum of antibacterial activity against both gram positive and gram negative organisms such as *Staphylococcus aureus, Salmonella schottmuelleri, Klebsiella pneumoniae, Proteus rettgeri, Escherichia coli, Streptococcus pyogenes,* etc. In particular, it has been found that the L-isomer of the compounds of formula I wherein $R_2$ is hydrogen are surprisingly active against beta-lactamase producing organisms such as Enterobacter, indole-positive Proteus, resistant *Escherichia coli,* and Serratia.

The compounds of formula I can be used as antibacterial agents in a prophylactic manner, e.g., in cleaning or as surface disinfecting compositions, or otherwise to combat infections due to organisms such as those named above, and in general may be utilized in a manner similar to cephalothin and other cephalosporins. For example, a compound of formula I or a physiologically acceptable salt thereof may be used in various animal species in an amount of about 1 to 100 mg./kg., daily, orally or parenterally, in single or two to four divided doses to treat infections of bacterial origin, e.g., 5.0 mg./kg. in mice.

Up to about 600 mg. of a compound of formula I or a physiologically acceptable salt thereof may be incorporated in an oral dosage form such as tablets, capsules or elixirs or in an injectable form in a sterile aqueous vehicle prepared according to conventional pharmaceutical practice.

They may also be used in cleaning or disinfecting compositions, e.g., for cleaning barns or dairy equipment, at a concentration of about 0.2 to 1% by weight of such compounds admixed with, suspended or dissolved in conventional inert dry or aqueous carriers for application by washing or spraying.

They are also useful as nutritional supplements in animal feeds.

Illustrative process details are provided in the examples for the various reactions. All temperatures are on the centigrade scale.

EXAMPLE 1

7β-[[[(Aminocarbonyl)amino](D-phenyl)acetyl]amino]-3-[[(1-methyl-1H-tetrazol-5-yl)thio]methyl]-8-oxo-5-thia-1-azabicyclo-[4.2.0]oct-2-ene-2-carboxylic acid a) Ethyl acetate adduct of 7-amino-3-[[(1-methyl-1H-tetrazol-5-yl)thio]-methyl]-8-oxo-5-thia-1-azabicyclo[4.2.0]oct-2-ene-2-carboxylic acid, 4-methylbenzenesulfonic acid salt 32.8 g. of 7-amino-3-[[(1-methyl-1H-tetrazol-5-yl)thio]-8-oxo-5-thia-1-azabicyclo[4.2.0]oct-2-ene-2-carboxylic acid (produced from 7-aminocephalosporanic acid by treatment with 1-methyl-tetrazole-5-thiol at 60° C at a pH of 7.5–8.0 in water/acetone) are finely pulverized and suspended in a mixture of 700 ml. of anhydrous dioxane and 575 ml. of anhydrous methanol. 20.6 g. of 4-methylbenzenesulfonic acid monohydrate are added to the suspension with vigorous stirring. After 30 minutes a clear solution results, which is then concentrated on a rotary evaporator. In order to completely remove water from the residue, 200 ml. of anhydrous dioxane are added and the solution again concentrated. This procedure is repeated twice more. The oily residue crystallizes upon trituration with ethyl acetate. 61.2 g. of the ethyl acetate adduct of 7-amino-3-[[(1-methyl-1H-tetrazol-5-yl)thio]methyl]-8-oxo-5-thia-1-azabicyclo[4.2.0]-oct-2-ene-2-carboxylic acid, 4-methylbenzenesulfonic acid salt are obtained.

b) 7-Amino-3-[[(1-methyl-1H-tetrazol-5-yl)thio]methyl]-8-oxo-5-thia-1-azabicyclo[4.2.0]oct-2-ene-2-carboxylic acid, diphenylmethyl ester The product from part (a) is suspended in a mixture of 700 ml. dioxane and 300 ml. of ethyl acetate. To this mixture is added dropwise at 10°–15° with vigorous stirring a solution of diphenyldiazomethane [produced from 40 g. of benzophenone hydrazone and 43.7 g. of mercuric oxide by stirring vigorously for 6 hours with 220 ml. of petroleum ether (b.p. 40 to 60°), filtering and concentrating] in 200 ml. of anhydrous dioxane. After stirring for 3 hours at room temperature a clear, wine red solution results, which is treated with 75 ml. of methanol to remove excess diphenyldiazomethane. After the wine red color disappears, the yellow brown solution is concentrated, the residue is dissolved in 800 ml. of methylene chloride and the solution is washed with a solution of 40 g. of dibasic potassium phosphate in 800 ml. of water and then with 400 ml. of water, dried with magnesium sulfate and concentrated. The viscous residue is triturated with petroleum ether. 47.7 g. of 7-amino-3-[[(1-methyl-1H-tetrazol-5-yl)thio]methyl]-8-oxo-5-thia-1-azabicyclo-[4.2.0]oct-2-ene-2-carboxylic acid, diphenylmethyl ester are obtained. The crude product is purified by stirring for 1 hour with 50 ml. of ice cold ethyl acetate and filtered under suction, to yield 28.5 g. of purified product, m.p. 153°–156° (dec.). The product is recrystallized from methylene chloride/petroleum ether, m.p. 166°–168° (dec.).

c) D-α-[[[(4-Methoxyphenyl)methoxy]carbonyl]amino]phenylacetic acid

D-Phenylglycine and magnesium oxide are suspended in water. To this suspension is added a solution of (p-methoxyphenyl)methoxycarbonylazide in dioxane. The mixture is stirred at room temperature, filtered, and the filtrate is extracted with ether. The aqueous phase is layered over with ethyl acetate, washed with water, dried, and concentrated to obtain D-α-[[[(4-methoxyphenyl)methoxy]carbonyl]amino]phenylacetic acid.

d) 7β-[[[[(4-Methoxyphenyl)methoxy]carbonyl]amino](D-phenyl)-acetyl]amino]-3-[[(1-methyl-1H-tetrazol-5-yl)thio]methyl]-8-oxo-5-thia-1-azabicyclo[4.2.0]oct-2-ene-2-carboxylic acid, diphenylmethyl ester 4.95 g. (0.01 mol.) of 7-amino-3-[[(1-methyl-1H-tetrazol-5-yl)thio]methyl]-8-oxo-5-thia-1-azabicyclo[4.2.0]-oct-2-ene-2-carboxylic acid, diphenylmethyl ester from part (b) and 3.78 g. (0.012 mol.) of D-β-[[[(4-methoxyphenyl)methoxy]-carbonyl]amino]phenylacetic acid from part (c) are suspended in a mixture of 100 ml. of tetrahydrofuran and 50 ml. of methylene chloride. To this suspension are added dropwise at 0°–5° C over a period of 1 hour 2.27 g. (0.011 mol.) of dicyclohexylcarbodiimide dissolved in 40 ml. of absolute tetrahydrofuran. This mixture is stirred for 90 minutes at 0°–5° C (the solution becomes almost clear after about 30 minutes, then it again becomes turbid as the dicyclohexylurea precipitates) and 90 minutes at room temperature. The dicyclohexylurea is filtered off and the filtrate is concentrated. The residue is dissolved in 800 ml. of ethyl acetate and the solution is shaken twice with 1N sodium bicarbonate solution and twice with water. the solution is then treated with activated carbon, dried with magnesium sulfate, filtered and concentrated to a volume of approximately 100 ml. 5.5 g. of 7β-[[[[(4-methoxyphenyl)-methoxy]carbonyl]-amino](D-phenyl)acetyl]amino]-3-[[(1-methyl-1H-tetrazol-5-yl)thio]methyl]-8-oxo-5-thia-1-azabicyclo[4.2.0]-oct-2-ene-2-carboxylic acid, diphenylmethyl ester crystallize, the compound begins to decompose at 143° C.

e) 7β-[[(α-Amino-D-phenyl)acetyl]amino]-3-[[(1-methyl-1H-tetrazol-5-yl)thio]methyl]-8-oxo-5-thia-1-azabicyclo[4.2.0]-oct-2-ene-2-carboxylic acid, trifluoroacetic acid salt 3.8 g. of 7β-[[[[(4-methoxyphenyl)methoxy]carbonyl]-amino](D-phenyl)acetyl]amino]-3-[[(1-methyl-1H-tetrazol-5-yl)-thio]methyl]-8-oxo-5-thia-1-azabicyclo[4.2.0]oct-2-ene-2-carboxylic acid, diphenylmethyl ester from part (d) are added at 0°–5° C to a mixture of 76 ml. of trifluoroacetic acid and 22.8 ml. of anisole. After 10 minutes, the solvent is evaporated under vacuum. The residue, upon trituration with ether, solidifies to yield 2.85 g. of 7β-[[(α-amino-D-phenyl)acetyl]-amino]-3-[[(1-methyl-1H-tetrazol-5-yl)thio]methyl]-8-oxo-5-thia-1-azabicyclo[4.2.0]oct-2-ene-2-carboxylic acid, trifluoroacetic acid salt, which decomposes above 126° C.

f) 7β-[[[(Aminocarbonyl)amino](D-phenyl)acetyl]-amino]-3-[[(1-methyl-1H-tetrazol-5-yl)thio]methyl]-8-oxo-5-thia-1-azabicyclo[4.2.0]oct-2-ene-2-carboxylic acid 0.25 g. (0.003 mol.) of potassium cyanate are dissolved in 6 ml. of water and to the solution are added 0.86 g. (0.0015 mol.) of 7β-[[(α-amino-D-phenyl)acetyl]amino]-3-[[(1-methyl-1H-tetrazol-5-yl)thio]methyl]-8-oxo-5-thia-1-azabicyclo[4.2.0]oct-2-ene-2-carboxylic acid, trifluoroacetic acid salt from part (e). This mixture is stirred at room temperature and after about 15 minutes, the solution becomes practically clear. The solution is stirred at room temperature for a total of about three hours, filtered, and the filtrate is acidified to pH 1.5 with 2N hydrochloric acid. The resulting precipitate is filtered under suction and washed with water, to yield 0.6 g. of 7β-[[[(amino-carbonyl)amino](D-phenyl)acetyl]amino]-3-[[(1-methyl-1H-tetrazol-5-yl)thio]methyl]-8-oxo-5-thia-1-azabicyclo[4.2.0]oct-2-ene-2-carboxylic acid, m.p. 163°–165° C (dec.).

EXAMPLE 2

7β-[[[(Aminocarbonyl)amino](D-phenyl)acetyl]amino]-3-[[(1-methyl-1H-tetrazol-5-yl)thio]methyl]-8-oxo-5-thia-1-azabicyclo[4.2.0]oct-2-ene-2-carboxylic acid, potassium salt An equimolar aqueous solution of the final product from example 1 and potassium bicarbonate is freeze-dried to yield as a powder 7β-[[[(aminocarbonyl)amino](D-phenyl)acetyl]-amino]-3-[[(1-methyl-1H-tetrazol-5-yl)thio]methyl]-8-oxo-5-thia-1-azabicyclo[4.2.0-]oct-2-ene-2-carboxylic acid, potassium salt.

Similarly, by substituting sodium bicarbonate for the potassium bicarbonate, one obtains the corresponding sodium salt.

EXAMPLE 3

7β-[[[(Aminocarbonyl)amino](L-phenyl)acetyl]amino]-3-[[(1-methyl-1H-tetrazol-5-yl)thio]methyl]-8-oxo-5-thia-1-azabicyclo-[4.2.0]oct-2-ene-2-carboxylic acid a) L-α-[[[(4-Methoxyphenyl)methoxy]carbonyl]amino]-phenylacetic acid L-Phenylglycine (obtained from D,L-phenylglycine by the method of Nishimura et al., Chem. Abst., Vol. 58, p. 11464f) and magnesium oxide are suspended in water and reacted with a solution of (p-methoxyphenyl)methoxycarbonylazide in dioxane according to the procedure of example 1(c) to yield L-α-[[[(4-methoxyphenyl)methoxy]carbonyl]amino]phenylacetic acid.

b) 7β-[[[[[(4-Methoxyphenyl)methoxy]carbonyl]amino](L-phenyl)-acetyl]amino]-3-[[(1-methyl-1H-tetrazol-5-yl)thio]methyl]-8-oxo-5-thia-1-azabicyclo[4.2.0]oct-2-ene-2-carboxylic acid, diphenylmethyl ester 7-Amino-3-[[(1-methyl-1H-tetrazol-5-yl)thio]methyl]-8-oxo-5-thia-1-azabicyclo[4.2.0]oct-2-ene-2-carboxylic acid, diphenylmethyl ester from example 1(b) and L-α-[[[(4-methoxyphenyl)methoxy]carbonyl]amino]phenylacetic acid from part (a) are reacted in the presence of dicyclohexylcarbodiimide according to the procedure of example 1(d) to yield 7β-[[[[[(4-methoxyphenyl)methoxy]carbonyl]amino](L-phenyl)-acetyl]amino]-3-[[(1-methyl-1H-tetrazol-5-yl)thio]methyl]-8-oxo-5-thia-1-azabicyclo[4.2.0]oct-2-ene-2-carboxylic acid, diphenylmethyl ester; m.p. 117° (dec.).

c) 7β-[[(α-Amino-L-phenyl)acetyl]amino]-3-[[(1-methyl-1H-tetrazol-5-yl)thio]methyl]-8-oxo-5-thia-1-azabicyclo acid, trifluoroacetic acid salt The diphenylmethyl ester product from part (b) is treated with trifluoroacetic acid and anisole according to the procedure of example 1(e) to yield 7β-[[(α-amino-L-phenyl)acetyl]amino]-3-[[(1-methyl-1H-tetrazol-5-yl)thio]-methyl]-8-oxo-5-thia-1-azabicyclo[4.2.0]oct-2-ene-2-carboxylic acid, trifluoroacetic acid salt.

d) 7β-[[[(Aminocarbonyl)amino](L-phenyl)acetyl]amino]-3-[[(1-methyl-1H-tetrazol-5-yl)thio]methyl]-8-oxo-5-thia-1-azabicyclo[4.2.0]oct-2-ene-2-carboxylic acid The trifluoroacetic acid salt product from part (c) is reacted with potassium cyanate according to the procedure of example 1(f) to yield 7β-[[[(aminocarbonyl)amino](L-phenyl)acetyl]amino]-3-[[(1-methyl-1H-tetrazol-5-yl)thio]methyl]-8-oxo-5-thia-1-azabicyclo[4.2.0]oct-2-ene-2-carboxylic acid, m.p. 156° (dec.).

An aqueous equimolar solution of this acid and potassium bicarbonate is freeze-dried to yield 7β-[[[(aminocarbonyl)-amino]-amino](L-phenyl)acetyl]amino]-3-[[(1-methyl-1H-tetrazol-5-yl)-thio]methyl]-8-oxo-5-thia-1-azabicyclo [4.2.0]oct-2-ene-2-carboxylic acid, potassium salt; m.p. 174° (dec.).

Similarly, by substituting sodium bicarbonate for the potassium bicarbonate one obtains the corresponding sodium salt.

EXAMPLE 4

7β-[[[(Aminocarbonyl)amino](L-4-hydroxyphenyl)acetyl]amino]-3-[[(1-methyl-1H-tetrazol-5-yl)thio]methyl]-8-oxo-5-thia-1-azabicyclo-[4.2.0]oct-2-ene-2-carboxylic acid a) L-α-[[[(4-Methoxyphenyl)methoxy]carbonyl]amino]-4-hydroxyphenylacetic acid 26 g. of L-(4-hydroxyphenyl)glycine are suspended in water and brought into solution by the addition of triethylamine. A solution of (p-methoxyphenyl)methoxycarbonylazide in dioxane is added with stirring. The mixture is stirred for an additional hour at room temperature and dioxane is then evaporated under vacuum. The aqueous phase is cooled to 0°, layer over with ethyl acetate and acidified to pH 2.5 with 2N hydrochloric acid. The aqueous phase is extracted twice more with ethyl acetate, the combined ethyl acetate extracts are dried with magnesium sulfate and concentrated under vacuum. The residue is recrystallized from ethyl acetate-petroleum ether to yield L-α-[[[(4-methoxyphenyl)methoxy]carbonyl]amino]-4-hydroxyphenylacetic acid; m.p. 133°–134° (dec.); $[\alpha]_D^{20} = +105.2°$ (c=1, tetrahydrofuran).

b) 7β-[[[[[(4-Methoxyphenyl)methoxy]carbonyl]amino](L-4-hydroxyphenyl)acetyl]amino]-3-[[(1-methyl-1H-tetrazol-5-yl)thio]-methyl]-8-oxo-5-thia-1-azabicyclo[4.2.0]oct-2-ene-2-carboxylic acid, diphenylmethyl ester 4.94 g. (0.01 mole) of 7-amino-3-[[(1-methyl-1H-tetrazol-5-yl)thio]methyl]-8-oxo-5-thia-1-azabicyclo [4.2.0]-oct-2-ene-2-carboxylic acid, diphenylmethyl ester from example 1(b) and 4.14 g. (0.0125 mole) of L-α-[[[(4-methoxyphenyl)methoxy]carbonyl]amino]-4-hydroxyphenylacetic acid from part (a) are reacted with 2.72 g. (0.0125 mole) of dicyclohexylcarbodiimide according to the procedure of example 1(d) to yield 8.2 g. of 7β-[[[[[(4-methoxyphenyl)-methoxy]carbonyl]amino](L-4-hydroxyphenyl)acetyl]amino]-3-[[(1-methyl-1H-tetrazol-5-yl)thio]methyl]-8-oxo-5-thia-1-azabicyclo[[4.2.0]oct-2-ene-2-carboxylic acid, diphenylmethyl ester; m.p. 120°–122° (dec.).

c) 7β-[[(α-Amino-L-4-hydroxyphenyl)acetyl]amino]-3-[[(1-methyl-1H-tetrazol-5-yl)thio]methyl-8-oxo-5-thia-1-azabicyclo-[4.2.0]oct-2-ene-2-carboxylic acid, trifluoroacetic acid salt 2.6 g. of the diphenylmethyl ester product from part (b) are treated with trifluoroacetic acid and anisole according to the procedure of 1(e) to yield 1.9 g. of 7β-[[(α-amino-L-4-hydroxyphenyl)acetyl]amino]-3-[[(1-methyl-1H-tetrazol-5-yl)-thio]methyl]-8-oxo-5-thia-1-azabicyclo[4.2.0]oct-2-ene-2-carboxylic acid, trifluoroacetic acid salt; m.p. about 145° (dec.).

d) 7β-[[[(Aminocarbonyl)amino](L-4-hydroxyphenyl)acetyl]amino]-3-[[(1-methyl-1H-tetrazol-5-yl)thio]methyl]-8-oxo-5-thia-1-azabicyclo[4.2.0]oct-2-ene-2-carboxylic acid The trifluoroacetic acid salt product from part (c) is reacted with potassium cyanate according to the procedure of example 1(f) to yield 7β-[[[(aminocarbonyl)amino]-(L-4-hydroxyphenyl)acetyl]amino]-3-[[(1-methyl-1H-tetrazol-5-yl)-thio]methyl]-8-oxo-5-thia-1-azabicyclo[4.2.0]oct-2-ene-2-carboxylic acid; m.p. about 172° (dec.).

An equimolar solution of this acid and sodium bicarbonate is freeze-dried to yield 7β-[[[(aminocarbonyl)amino](L-4-hydroxyphenyl)acetyl]amino]-3-[[(1-methyl-1H-tetrazol-5-yl)-thio]methyl]-8-oxo-5-thia-1-azabicyclo[4.2.0]oct-2-ene-2-carboxylic acid, sodium salt; m.p. about 130° (dec.).

In a similar manner, the corresponding potassium salt can be obtained.

EXAMPLE 5

7β-[[[(Aminocarbonyl)amino](D-4-hydroxyphenyl)acetyl]amino]-3-[[(1-methyl-1H-tetrazol-5-yl)thio]methyl]-8-oxo-5-thia-1-azabicyclo[4.2.0]oct-2-ene-2-carboxylic acid Following the procedure of example 4 but substituting D-(4-hydroxyphenyl)glycine for the L-isomer in part (a), one obtains 7β-[[[(aminocarbonyl)amino](D-4-hydroxyphenyl)acetyl]-amino]-3-[[(1-methyl-1H-tetrazol-5-yl)thio]methyl]-8-oxo-5-thia-1-azabicyclo[4.2.0]oct-2-ene-2-carboxylic acid; m.p. 165°.

An aqueous equimolar solution of this acid and sodium bicarbonate is freeze-dried to yield 7β-[[[-(aminocarbonyl)amino]-(D-4-hydroxyphenyl)acetyl]-amino]-3-[[(1-methyl-1H-tetrazol-5-yl)thio]methyl]-8-oxo-5-thia-1-azabicyclo[4.2.0]oct-2-ene-2-carboxylic acid, sodium salt, hydrate; m.p. 215°.

In a similar manner, one can obtain the corresponding potassium salt.

EXAMPLES 6–30

Similarly, following the procedure of example 1 but substituting for the D-phenylglycine in part (c) the compound in Col. A one obtains the product in Col. B.

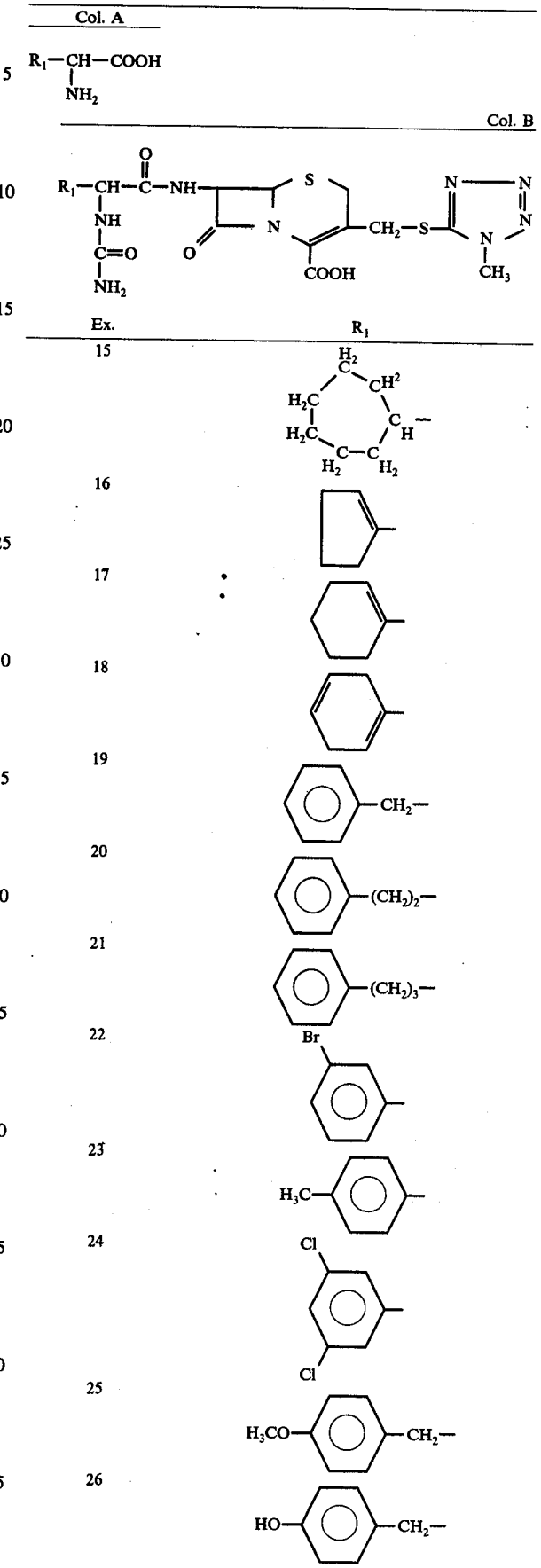

-continued

| Col. A | Col. B |
|---|---|
| 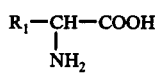 | 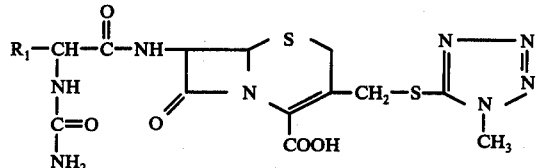 |

| Ex. | $R_1$ |
|---|---|
| 27 | 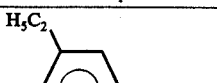 |
| 28 | 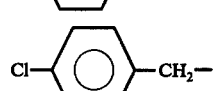 |
| 29 | 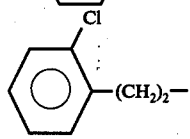 |

The compounds of Col. A may be in either the D- or L- or D,L-isomeric form.

EXAMPLE 30

7β-[[[(Aminocarbonyl)amino](D-phenyl)acetyl]amino]-3-[[(5-methyl-1,3,4-thiadiazol-2-yl)thio]methyl]-8-oxo-5-thia-1-azabicyclo[4.2.0]oct-2-ene-2-carboxylic acid a) 7-Amino-3-[[(5-methyl-1,3,4-thiadiazol-2-yl)thio]methyl]-8-oxo-5-thia-1-azabicyclo[4.2.0]oct-2-ene-2-carboxylic acid, diphenylmethyl ester 18 g. of 7-amino-3-[[(5-methyl-1,3,4-thiadiazol-5-yl)thio]methyl]-8-oxo-5-thia-1-azabicyclo[4.2.0]oct-2-ene-2-carboxylic acid are suspended in 350 ml. of tetrahydrofuran. 4.1 ml. of 70% perchloric acid are added dropwise. After 30 minutes, a slightly turbid solution forms. This solution is filtered and to the filtrate is added dropwise with stirring 12 g. of diphenyldiazomethane and 20 ml. of tetrahydrofuran. After 3 hours, the reaction mixture is poured into 2 liters of absolute ether. The solid, light brown precipitate, which is the perchloric acid salt of the desired product, is dried over Kieselgel in a desiccator. To obtain the base, the perchloric acid salt is dissolved in water and treated with the calculated equivalent of potassium bicarbonate. The aqueous solution obtained is extracted with chloroform. The chloroform phase is treated with activated carbon and sodium sulfate to obtain 10 g. of the product, 7-amino-3-[[(5-methyl-1,3,4-thiadiazol-2-yl)thio]methyl]-8-oxo-5-thia-1-azabicyclo[4.2.0]oct-2-ene-2-carboxylic acid, diphenylmethyl ester, as a light brown powder, m.p. 157°–159°. The product is recrystallized from tetrahydrofuran/petroleum ether.

b) 7β-[[[(Aminocarbonyl)amino](D-phenyl)acetyl]amino]-3-[[(5-methyl-1,3,4-thiadiazol-2-yl)thio]methyl]-8-oxo-5-thia-1-azabicyclo[4.2.0]oct-2-ene-2-carboxylic acid Following the procedure of example 1, part (d), (e), and (f) but employing the 7-amino-3-[[(5-methyl-1,3,4-thiadiazol-2-yl)thio]methyl]-8-oxo-5-thia-1-azabicyclo[4.2.0]-oct-2-ene-2-carboxylic acid, diphenylmethyl ester from part (a) in example 1(d) one obtains the titled product.

EXAMPLES 31–80

Following the procedure of example 1 but employing the 7-aminocephalosporanic acid derivatives shown in Col. A the products shown in Col. B are obtained

| Col. A | Col. B |
|---|---|
| 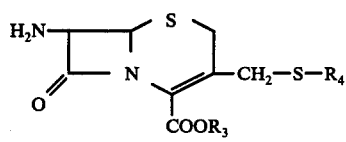 | 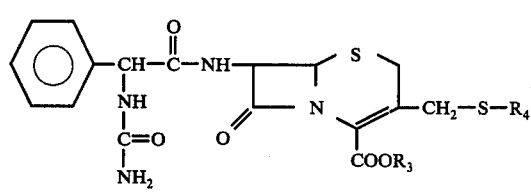 |

| Ex. | $R_3$ | $R_4$ |
|---|---|---|
| 31 | H | 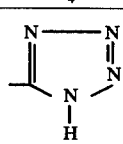 |
| 32 | H | 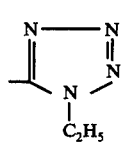 |

-continued

| | Col. A | Col. B |
|---|---|---|
| Ex. | R₃ | R₄ |
| 33 | H | tetrazole-N-C₃H₇ |
| 34 | H | tetrazole-N-C₄H₉ |
| 35 | CH(C₆H₅)₂ | tetrazole-N-C₂H₅ |
| 36 | t-C₄H₉ | tetrazole-N-CH₃ |
| 37 | —CH₂—C₆H₅ | tetrazole-N-CH₃ |
| 38 | —CH₂—C₆H₄—Cl | tetrazole-N-CH₃ |
| 39 | —CH₂—C₆H₄—CH₃ | tetrazole-N-C₂H₅ |
| 40 | —CH₂—O—C(O)—CH₃ | tetrazole-N-CH₃ |
| 41 | —CH₂—O—C(O)—CH₂—C₆H₅ | tetrazole-N-H |

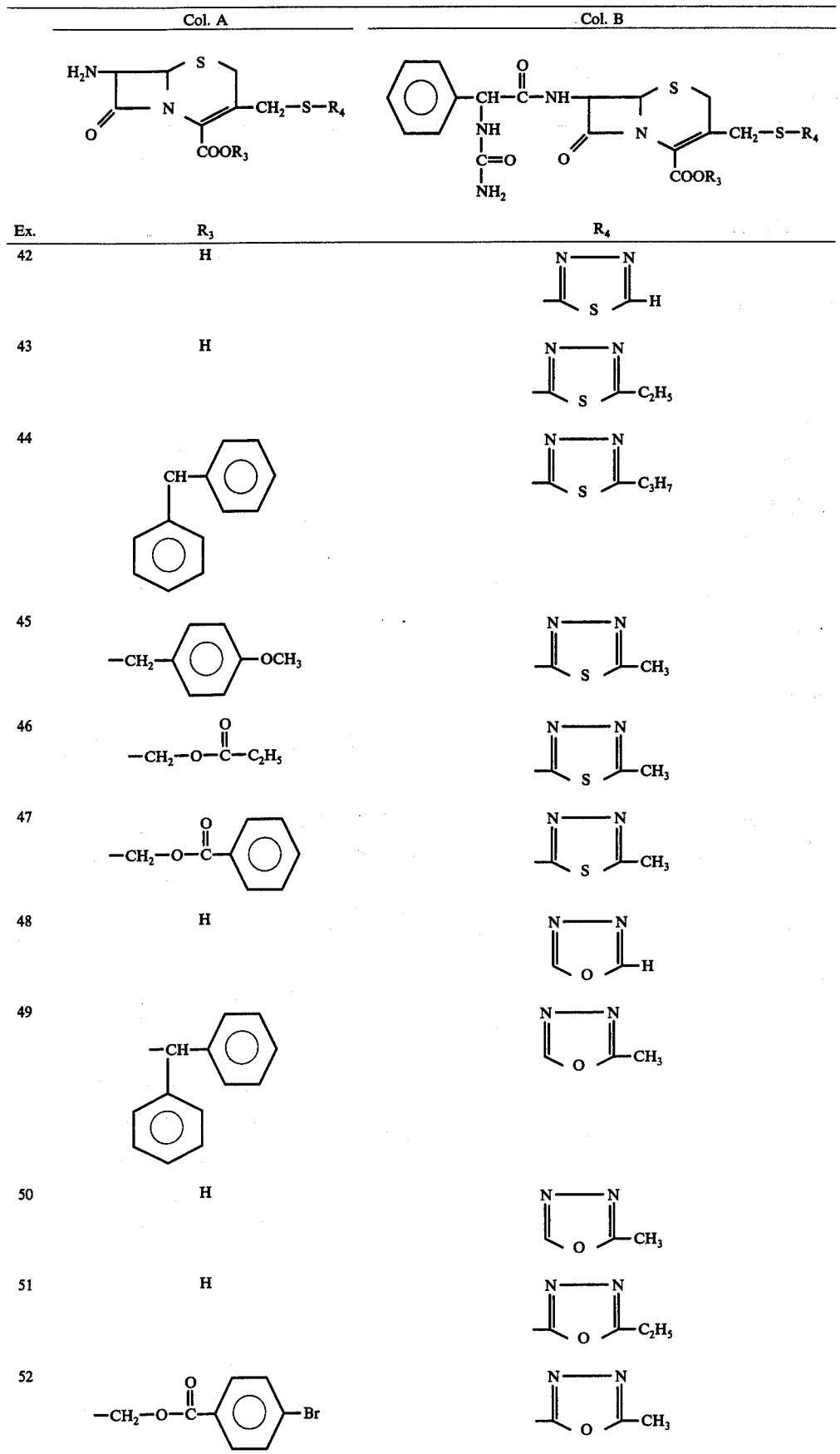

-continued

| Ex. | R₃ (Col. A) | R₄ (Col. B) |
|---|---|---|
| 53 | -CH₂-O-C(=O)-CH₂-C₆H₄(OCH₃) | 2-methyl-1,3,4-oxadiazol-5-yl |
| 54 | -CH(C₆H₅)₂ | 1,3,4-thiadiazol-2-yl (H) |
| 55 | -CH(C₆H₅)₂ | 5-methyl-1,3,4-thiadiazol-2-yl |
| 56 | H | 5-methyl-1,3,4-thiadiazol-2-yl |
| 57 | -CH₂-O-C(=O)-CH₃ | 5-ethyl-1,3,4-thiadiazol-2-yl |
| 58 | -CH(C₆H₅)₂ | 1,2,3,4-thiatriazol-5-yl |
| 59 | H | 1,2,3,4-thiatriazol-5-yl |
| 60 | t-C₄H₉ | thiazol-2-yl |
| 61 | H | 4-methyl-thiazol-2-yl |
| 62 | H | 5-methyl-thiazol-2-yl |
| 63 | H | 4-propyl-thiazol-2-yl |

-continued

| | Col. A | Col. B |
|---|---|---|
| Ex. | R₃ | R₄ |
| 64 | -CH(C₆H₅)₂ | isoxazole (H, H) |
| 65 | H | 3-methylisoxazole |
| 66 | H | 5-methylisoxazole |
| 67 | H | 5-ethylisoxazole |
| 68 | -CH(C₆H₅)₂ | pyridine N-oxide |
| 69 | H | pyridine N-oxide |
| 70 | Si(CH₃)₃ | 1-methyltetrazole |
| 71 | Sn(CH₃)₃ | 5-methyl-1,3,4-thiadiazole |
| 72 | Si(C₂H₅)₃ | 5-methyl-1,3,4-thiadiazole |
| 73 | Sn(C₂H₅)₃ | 1-methyltetrazole |

-continued

| | Col. A | Col. B |
|---|---|---|
| | H₂N-[β-lactam-S ring]-CH₂-S-R₄, COOR₃ | Phenyl-CH(NH-C(=O)-NH₂)-C(=O)-NH-[β-lactam-S ring]-CH₂-S-R₄, COOR₃ |

| Ex. | R₃ | R₄ |
|---|---|---|
| 74 | Ca/2 | 1-methyl-1H-tetrazol-5-yl |
| 75 | Mg/2 | 2-methyl-1,3,4-thiadiazol-5-yl |
| 76 | Na | 2-methyl-1,3,4-thiadiazol-5-yl |
| 77 | Na | 1-ethyl-1H-tetrazol-5-yl |
| 78 | Al/3 | 1-methyl-1H-tetrazol-5-yl |
| 79 | [CH₃NH₃]⊕ | 1-methyl-1H-tetrazol-5-yl |
| 80 | [(C₆H₅CH₂)₂NH₂]⊕ | 2-methyl-1,3,4-thiadiazol-5-yl |

By also employing the substituted glycine compounds from examples 3–30, in place of the D-phenylglycine in example 1 other compounds within the scope of the invention are obtained.

EXAMPLES 81–88

Following the procedure of example 1 but substituting for the potassium cyanate in part (f) one of the following:

methylisocyanate
ethylisocyanate
propylisocyanate
i-propylisocyanate
butylisocyanate
i-butylisocyanate
t-butylisocyanate
pentylisocyanate one obtains:

7β-[[[(methylaminocarbonyl)amino](D-phenyl)acetyl]amino]-3-[[(1-methyl-1H-tetrazol-5-yl)thio]methyl]-8-oxo-5-thia-1-azabicyclo[4.2.0]oct-2-ene-2-carboxylic acid;

7β-[[[(ethylaminocarbonyl)amino](D-2-phenyl)acetyl]amino]-3-[[(1-methyl-1H-tetrazol-5-yl)thio]methyl]-8-oxo-5-thia-1-azabicyclo[4.2.0]oct-2-ene-2-carboxylic acid;

7β-[[[(propylaminocarbonyl)amino](D-2-phenyl)acetyl]amino]-3-[[(1-methyl-1H-tetrazol-5-yl)thio]methyl]-8-oxo-5-thia-1-azabicyclo[4.2.0]oct-2-ene-2-carboxylic acid;

7β-[[[(i-propylaminocarbonyl)amino](D-2-phenyl)acetyl]-amino]-3-[[(1-methyl-1H-tetrazol-5-yl)thio]methyl]-8-oxo-5-thia-1-azabicyclo[4.2.0]oct-2-ene-2-carboxylic acid;

7β-[[[(butylaminocarbonyl)amino](D-2-phenyl)acetyl]-amino-]-3-[[(1-methyl-1H-tetrazol-5-yl)thio]-methyl]-8-oxo-5-thia-1-azabicyclo[4.2.0]oct-2-ene-2-carboxylic acid;

7β-[[[(i-butylaminocarbonyl)amino](D-2-phenyl)acetyl]-amino]-3-[[(1-methyl-1H-tetrazol-5-yl)thio]methyl]-8-oxo-5-thia-1-azabicyclo[4.2.0]oct-2-ene-2-carboxylic acid;

7β-[[[(t-butylaminocarbonyl)amino](D-2-phenyl)acetyl]-amino]-3-[[(1-methyl-1H-tetrazol-5-yl)thio]methyl]-8-oxo-5-thia-1-azabicyclo[4.2.0]oct-2-ene-2-carboxylic acid;
and 7β-[[[(pentylaminocarbonyl)amino](D-2-phenyl)acetyl]-amino]-3-[[(1-methyl-1H-tetrazol-5-yl)thio]methyl]-8-oxo-5-thia-1-azabicyclo[4.2.0]oct-2-ene-2-carboxylic acid respectively.

Similarly, these alkylisocyanates can be employed in the procedures of examples 3 to 80 to obtain other compounds within the scope of this invention.

What is claimed is:

1. A compound of the formula:

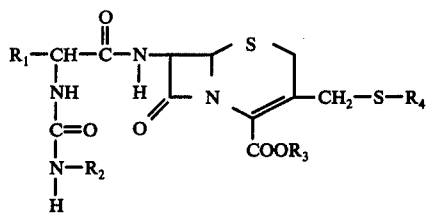

wherein $R_1$ is selected from the group consisting of phenyl, benzyl, phenethyl, and monosubstituted phenyl, benzyl, and phenethyl wherein said substituent is one member selected from the group consisting of Cl, Br, alkyl of 1 to 4 carbons, hydroxy, and alkoxy of 1 to 4 carbons; $R_2$ is straight or branched chain alkyl of 1 to 4 carbons; $R_3$ is selected from the group consisting of hydrogen, alkyl of 1 to 4 carbons, benzyl, phenethyl, diphenylmethyl, trimethylsilyl, trimethylstannyl, aluminum, an alkaline earth metal, an alkali metal, and the group

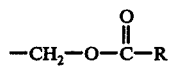

wherein R is selected from the group consisting of alkyl of 1 to 4 carbons, phenyl, benzyl, and phenethyl; and $R_4$ is selected from the group consisting of

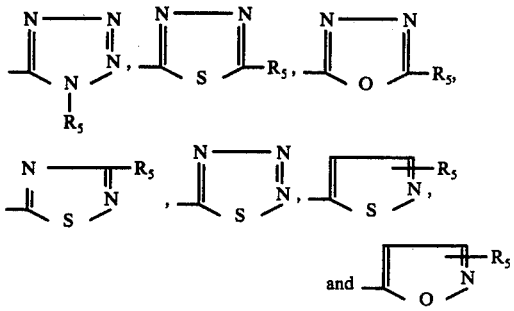

wherein $R_5$ is selected from the group consisting of hydrogen and alkyl of 1 to 4 carbons.

2. The compound of claim 1 as the D, L, or d,l-isomer wherein $R_1$ is phenyl or 4-hydroxyphenyl; and $R_3$ is hydrogen, potassium or sodium.

3. The compound of claim 2 wherein $R_4$ is

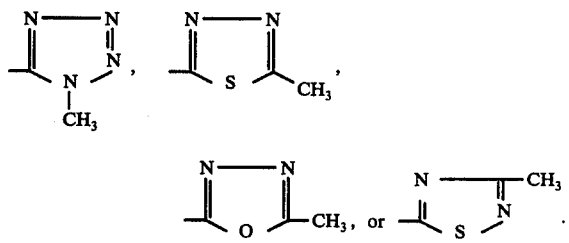

4. The compound of claim 3 wherein $R_4$ is

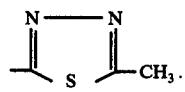

5. The compound of claim 4 wherein $R_2$ is methyl.
6. The compound of claim 3 wherein $R_4$ is

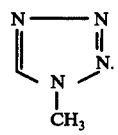

7. The compound of claim 6 wherein $R_2$ is methyl.
8. The compound of claim 7 wherein $R_1$ is phenyl and $R_3$ is hydrogen.

* * * * *

UNITED STATES PATENT AND TRADEMARK OFFICE
CERTIFICATE OF CORRECTION

PATENT NO. : 4,088,815
DATED : May 9, 1978
INVENTOR(S) : Hermann Breuer et al.

It is certified that error appears in the above-identified patent and that said Letters Patent are hereby corrected as shown below:

Col. 5, line 34, "formula VIII" should read -- formula VII --.

Signed and Sealed this

Seventh Day of November 1978

[SEAL]

Attest:

RUTH C. MASON
Attesting Officer

DONALD W. BANNER
Commissioner of Patents and Trademarks